(12) United States Patent
Vein

(10) Patent No.: US 6,835,390 B1
(45) Date of Patent: Dec. 28, 2004

(54) METHOD FOR PRODUCING TISSUE ENGINEERED MEAT FOR CONSUMPTION

(76) Inventor: Jon Vein, 101 N. Las Palmas Ave., Los Angeles, CA (US) 90004

( * ) Notice: Subject to any disclaimer, the term of this patent is extended or adjusted under 35 U.S.C. 154(b) by 268 days.

(21) Appl. No.: 09/991,544

(22) Filed: Nov. 16, 2001

Related U.S. Application Data

(60) Provisional application No. 60/249,993, filed on Nov. 17, 2000.

(51) Int. Cl.$^7$ .......................... A61K 47/00; A23L 1/31; C12N 11/14; C12N 11/08; C12N 5/06
(52) U.S. Cl. ..................... 424/439; 424/93.7; 426/7; 426/802; 435/176; 435/178; 435/180; 435/395
(58) Field of Search ................... 435/174, 178, 435/180, 395, 176, 177; 424/422, 423, 93.7, 439; 426/7, 802

(56) References Cited

U.S. PATENT DOCUMENTS

| | | | |
|---|---|---|---|
| 5,686,091 A | | 11/1997 | Leong et al. |
| 5,746,649 A | * | 5/1998 | Skaar et al. ............... 452/172 |
| 5,770,417 A | | 6/1998 | Vacanti et al. |
| 5,843,741 A | | 12/1998 | Wong et al. |
| 5,863,531 A | * | 1/1999 | Naughton et al. ......... 424/93.7 |
| 5,863,984 A | | 1/1999 | Doillon et al. |
| 5,916,265 A | | 6/1999 | Hu |
| 5,928,945 A | | 7/1999 | Seliktar et al. |
| 6,348,069 B1 | * | 2/2002 | Vacanti et al. ........... 623/11.11 |
| 6,592,623 B1 | * | 7/2003 | Bowlin et al. ........... 623/14.13 |

OTHER PUBLICATIONS

Ahrens, et al., "Expression of Human Bone Morphogenetic Proteins–2 or –4 in Murine Mesenchymal Progenitor C3H10T1/2 Cells Induces Differentiation into Distinct Mesenchymal Cell Lineages," *DNA Cell Biology* 1993; 12:871–880.

Grimaldi, et al., "Trans–differentiation of Myoblasts to Adipoblasts: Triggering Effects of Fatty Acids and Thiazolidinediones," *Prostglandins, Leukotrienes, and Essential Fatty Acids* 1997; 57(1):71–75.

Niklason, L., et al., "Advances in Tissue Engineering of Blood Vessels and Other Tissues," *Transplant Immunology* 1997; 5(4):303–306.

Sottile, V., et al., "Bone Morphogenetic Protein–2 Stimulates Adipogenic Differentiation of Mesenchymal Precursor Cells in Synergy with BRL 49653 9 (Rosiglitzaone)," *FEBS Letters* 2000; 475(3):201–204.

Teboul, et al., "Thiazolidinediones and Fatty Acids Convert Myogenic Cells into Adipose–Like Cells," *Journal of Biological Chemistry* 1995; 270(47):28183–28187.

Vacanti, J., et al., "Tissue Engineering: The Design and Fabrication of Living Replacement Devices for Surgical Reconstruction and Transplantation," *Lancet* 1999; 354 Suppl. 1:S132–S134.

Wang, et al., "Bone Morphogenetic Protein–2 Causes Commitment and Differentiation in C3H10T1/2 Cells," *Growth Factors* 1993; 9:57.

* cited by examiner

*Primary Examiner*—David M. Naff
(74) *Attorney, Agent, or Firm*—Perkins Coie LLP

(57) ABSTRACT

A non-human tissue engineered meat product and a method for producing such meat product are disclosed. The meat product comprises muscle cells that are grown ex vivo and is used for food consumption. The muscle cells may be grown and attached to a support structure and may be derived from any non-human cells. The meat product may also comprise other cells such as fat cells or cartilage cells, or both, that are grown ex vivo together with the muscle cells.

11 Claims, No Drawings

METHOD FOR PRODUCING TISSUE ENGINEERED MEAT FOR CONSUMPTION

RELATED APPLICATIONS

This application claims priority to U.S. Provisional Application No. 60/249,993 filed Nov. 17, 2000.

FIELD OF THE INVENTION

The field of the present invention relates to producing and harvesting meat products for consumption. In particular, it relates to tissue engineered meat for consumption.

BACKGROUND OF THE INVENTION

Meat products such as beef, pork, lamb, poultry, or fish are desirable products for food consumption. Meat products are currently produced from whole animals, which is a highly inefficient production method because a significant portion of all agriculturally produced grain is used for animal rather than human consumption. In the United States, for example, livestock feed accounts for approximately 70% of all the wheat, corn, and other grain produced. In addition, to produce one pound of beef, thousand of pounds of water are required for the animal to drink and to grow the livestock feed. Meanwhile, throughout the world, by some account, over 800 million people are malnourished and 50,000 people die of starvation every day.

Current meat production methods are also harmful to the environment. Rain forests are depleted at a rate of approximately 500 square feet of rain forest for every pound of beef to be grown. Likewise, modem techniques for fishing marine life have become so efficient that the oceans and lakes are over-fished. Species that were once common are now endangered or extinct.

Current scientific efforts to address these problems have focused on increasing the effectiveness of breeding or growing livestock. For example, growth hormones have been used to make livestock grow faster and thus, consume less grain and water. Growth hormones are typically injected into the livestock, but new methods of introducing the growth hormone have also been developed using genetic engineering technologies such as transgenics or cloning of the whole animal. Current meat production methods, nonetheless, require water, grain, and land to raise livestock.

Another problem with current meat production methods involves food contamination. Every year, on average, each American becomes sick and 9,000 people die from something they have injested. To control food contamination, the government's present strategy is to inspect meat during processing. The USDA and the FDA, however, rarely regulate the farms where pathogens originate because they lack the regulatory powers over the farms. Nonetheless, except for E. coli 0156:H7, dangerous bacteria are legally considered "inherent" to raw meat. Two of the "inherent bacteria," however,—campylobacter and salmonella—account for 80% of all illnesses and 75% of all deaths from meat and poultry consumption.

In the poultry industry, for example, as much as 25% of broiler chickens and 45% of ground chickens are reportedly allowed to test positive for salmonella. The Center for Disease Control estimates that campylobacter infects 70% to 90% of all chickens. Campylobacter infections cause cramps, bloody diarrhea, and fever. Every year in the United States, campylobacter infection results in about 800 deaths. Infections with campylobacter may also lead to Guillian-Barre syndrome, a disease that requires intensive care for several weeks. The incidence of serious illness and death from these bacteria may increase as more antibiotic-resistant strains develop. This has caused some scientists to question the continued use of antibiotics as a feed supplement for livestock.

Thus, there exists a need to produce meat products for consumption that is more efficient, safer, and healthier than the current methods of production.

SUMMARY OF THE INVENTION

The present invention is directed to tissue engineered meat products and methods for producing such meat products. In one embodiment of the invention, the meat product comprises muscle cells that are grown ex vivo. These muscle cells may be grown and attached to a support structure and may be derived from any non-human cells. In a preferred embodiment of the invention, the meat product is substantially free from any harmful microbial or parasitic contamination. Another embodiment of the invention is directed to a meat product comprising muscle cells and other cells such as fat cells or cartilage cells, or both, that are grown ex vivo together with the muscle cells. In another embodiment of the invention, the meat product comprises muscle cells that have been exposed to an electric or oscillating current.

GENERAL DESCRIPTION OF THE PREFERRED EMBODIMENT

Generally, meat products are taken from the muscles of animals. Butchers carve out corresponding cuts of beef, poultry, lamb, fish, or pork to be sold as steak, chicken breast, lamb chops, fish fillet, pork chops, etc. Meat products also include meat-product derivatives such as ground meat that may be processed into meatball, hamburger patty, fishball, sausage, salami, bologna, ham, etc. Meat products may also include muscle tissues or meat that has been seasoned or dried such as jerky.

One embodiment of the present invention involves a method for producing meat products that may be used for consumption. The method may include culturing muscle stem cells in vitro and allowing these cells to differentiate into specific types of muscle cells such as skeletal muscle cells or smooth muscle cells ex vivo. Muscle cells may be derived from any non-human animals consumed by humans such as mammals (e.g. cattle, buffalo, pigs, sheep, deer, etc.), birds (e.g. chicken, ducks, ostrich, turkey, pheasant, etc.), fish (e.g. swordfish, salmon, tuna, sea bass, trout, catfish, etc.), invertebrates (e.g. lobster, crab, shrimp, clams, oysters, mussels, sea urchin, etc.), reptiles (e.g. snake, alligator, turtle, etc.), and amphibians (e.g. frog legs). Preferably, muscle cells are derived from pluri-potent embryonic mesenchymal stem cells that give rise to muscle cells, fat cells, bone cells, and cartilage cells. The muscle cells may also be derived from toti-potent embryonic stem cells such as cells from the blastocyst stage, fertilized eggs, placenta, or umbilical cords of these animals.

Muscle cells may be grown in culture into muscle tissues that are attached to a support structure such as a two or three-dimensional scaffold or support structure. The muscle cells may be grown on the two dimensional support structure such as a petri-dish forming several layers of cells that may be peeled and processed for consumption. Other examples of two dimensional support structures may include porous membranes that allow for diffusion of nutrients from culture media on one side of the membrane to the other side where the cells are attached. In this type of culture conditions, additional layers of cells may be achieved by exposing the cells to culture media from both sides of the membrane, i.e., cells received nutrients through diffusion from one side of the membrane and also from the culture media covering the cells growing on the membrane.

Muscle cells may also be grown on, around, or inside a three-dimensional support structure. The support structure may be sculpted into different sizes, shapes, and forms, as desired, to provide the shape and form for the muscle cells to grow and resemble different types of muscle tissues such as steak, tenderloin, shank, chicken breast, drumstick, lamb chops, fish fillet, lobster tail, etc. The support structure may be made from natural or synthetic biomaterials that are preferably non-toxic so that they may not be harmful if ingested. Natural biomaterials may include, for example, collagen, fibronectin, laminin, or other extracellular matrices. Synthetic biomaterials may include, for example, hydroxyapatite, alginate, polyglycolic acid, polylactic acid, or their copolymers. The support structure may be formed as a solid or semisolid support.

To provide for optimal cell and tissue growth, the support structure, preferably, has high porosity to provide maximal surface area for cell attachment. A three-dimensional support structure may also be molded to include a branched vascular network providing for delivery of nutrients into and shuttling out of metabolites from the cells at the inner mass of the meat product. In this particular embodiment, the branch vascular network may be edible by using non-toxic natural or synthetic biomaterials as mentioned above. Furthermore, the support structure may also include adhesion peptides, cell adhesion molecules, or other growth factors covalently or non-covalently associated with the support structure. Examples of the peptides include sequences such as Arg-Gly-Asp or Arg-Glu-Asp-Val. Niklason, L., et. al., *Advances in Tissue Engineering of Blood Vessels and Other Tissues, Transplant Immunology,* 5(4):303–306 (1997). This reference is hereby incorporated by reference as if fully set forth herein.

On the other hand, culture conditions for these muscle cells may include static, stirred, or dynamic flow conditions. For scaled up production, the preferred method is to use a bioreactor, which produces greater volume of cells and allows greater control over the flow of nutrients, gases, metabolites, and regulatory molecules. Furthermore, bioreactors may provide physical and mechanical signals such as compression to stimulate cells to produce specific biomolecules. Vacanti, J., et. al., *Tissue Engineering: The Design and Fabrication of Living Replacement Devices for Surgical Reconstruction and Transplantation, Lancet,* 354 Suppl. 1, pSI32–34 (1999). This reference is hereby incorporated by reference as if fully set forth herein.

In another embodiment of the invention, meat products derived from muscle cells grown ex vivo may include fat cells derived also from any non-human animals. Fattier meat is generally tastier, but with greater fat content comes greater risk of adverse health consequences such as heart disease. Thus, the ratio of muscle cells to fat cells may be regulated in vitro to produce the meat products with optimal flavor and health effects. Regulation may be achieved by controlling the ratio of muscle and fat cells that are initially seeded in culture and/or by varying, as desired, the concentrations and ratio of growth factors or differentiation factors that act upon the muscle cells or fat cells.

In another embodiment of the invention, cartilage derived from chondrocytes may first form an underlying support layer or structure together with the support structure. Afterwards, muscle cells or fat cells, or both, may be seeded onto the chondrocyte layer. The interaction of muscle cells and chondrocytes may further provide the necessary regulatory signals required for tissue formation. Examples of meat products that have muscle cells and cartilage cells include chicken breast or pork ribs.

In a preferred embodiment of the invention, aseptic techniques may be used to culture the muscle cells resulting in meat products that are substantially free from harmful microbes such as bacteria, fungi, viruses, prions, protozoa, or any combination of the above. Harmful microbes may include pathogenic type microorganisms such as salmonella, campylobacter, *E. coli* 0156:H7, etc. In addition, muscle cells grown in culture may be substantially free from parasites such as tapeworms that infect muscles of whole animals and that are transferred to humans through consumption of insufficiently cooked meat. Aseptic techniques may also be employed in packaging the meat products as they come off the biological production line. Such quality assurance may be monitored by standard assays for microorganisms or chemicals that are already known in the art. "Substantially free" means that the concentration of microbes or parasites is below a clinically significant level of contamination, i.e., below a level wherein ingestion would lead to disease or adverse health conditions.

In another preferred embodiment of the invention, the meat product derived from muscle cells grown ex vivo may be exposed to an electric or oscillating current. Unlike muscle tissues derived from whole animals, muscle tissues grown ex vivo or in vitro may have never been exercised (e.g. never been used to move a leg). Thus, exposing the muscle cells, muscle tissue, or the meat products in vitro to an electric or oscillating current may mimic exercise and increase the similarity in texture between meat grown ex vivo and meat derived from whole animals. The electric or oscillating current may also increase the growth rate of muscle cells ex vivo. The electric or oscillating current may be applied to the muscle stem cells or to the muscle cells after they have differentiated from the stem cells.

In another embodiment of the invention, other nutrients such as vitamins that are normally lacking in meat products from whole animals may be added to increase the nutritional value of the meat. This may be achieved either through straight addition of the nutrients to the growth medium or through genetic engineering techniques. For example, the gene or genes for enzymes responsible for the biosynthesis of a particular vitamin, such as Vitamin D, A, or the different Vitamin B complexes, may be transfected in the cultured muscle cells to produce the particular vitamin.

In another embodiment of the invention, regulatory factors, growth factors, or other gene products may also be genetically introduced into the muscle cells. These factors, known as myogenic regulatory factors ("MRFs"), may stimulate and regulate the growth of muscles in vivo, but may not normally be produced by muscle cells in vivo or in vitro. Thus, expressing myogenic regulatory factors in cultured muscle cells may increase the production of muscle cells in vitro.

In another embodiment of the invention, the meat products derived from muscle cells in vitro may include different derivatives of meat products. These derivatives may be prepared, for example, by grounding or shredding the muscle tissues grown in vitro and mixed with appropriate seasoning to make meatballs, fishballs, hamburger patties, etc. The derivatives may also be prepared from layers of muscle cells cut and spiced into, for example, beef jerky, ham, bologna, salami, etc. Thus, the meat products of the present invention may be used to generate any kind of food product originating from the meat of an animal.

The following examples illustrate how one skilled in the art may make use of the current invention to produce meat products in vitro. Methods in cell biology, cell culture, and immunohistochemistry that are not explicitly described in this disclosure have already been amply reported in the scientific literature.

EXAMPLE I

This example illustrates the isolation of pluri-potent mesenchymal stem cells for use in producing meat products in vitro. Mesenchymal stem cells give rise to muscle cells (myocytes), fat cells (adipocytes), bone cells (osteocytes), and cartilage cells (chrondocytes). Mesenchymal stem cells may be dissected and isolated from embryonic tissues of any non-human animal embryos. In cattle, for example, embryonic mesenchymal tissues that are rich in pluri-potent muscle stem cells are preferably isolated from embryos at day 30 to 40 or earlier. Once dissected, the embryonic tissues may be minced into small pieces about one millimeter by one millimeter in size in phosphate buffered saline ("PBS") pH 7.45. Five to ten pieces of the minced tissue may be incubated in 300 µl of 0.25% trypsin and 0.1% EDTA in PBS for thirty minutes at 37° C. with gentle agitation. Afterwards, the tissues may be allowed to settle on the bottom of the tube by gravity or gentle centrifugation. The supernatant containing the trypsin/EDTA solution may then be aspirated and replaced with 300 µl of 0.1% collagenase in PBS for ten to thirty minutes at 37° C. Colleganese digestion may be repeated for several cycles as desired. Depending of the viscosity of the solution because of DNA released from damaged cells, 40 µl of DNase I at 1 mg/ml in PBS may be added to the collagenase solution in between cycles.

The reaction may be stopped by adding medium such as DMEM or Ham's F-12, or both in 1:1 ratio, (Life Technologies, Rockville, Md.) that is supplemented with 10 mM Hepes, 2 mM L-glutamine (Sigma-Aldrich), 10–20% heat-inactivated fetal calf or bovine serum (Hyclone Laboratories, Logan, Utah), penicillin at 100 units/ml and streptomycin at 100 µg/ml ("complete medium"). Cells may be completely dissociated by gently pipetting the tissues up and down followed by washing the cells in complete medium once or twice using a centrifuge. The cells may then be plated onto an appropriate-sized petri dish which may be coated with natural biomaterials (e.g. collagen, fibronectin, laminin, or other extracellular matrices) or synthetic biomaterials (e.g. hydroxyapatite, alginate, polyglycolic acid, polylactic acid, or their copolymers), or both, and may be grown at 37° C. and equilibrated with 5% $CO_2$.

EXAMPLE II

After mesenchymal stem cells have been isolated, they may be enriched for myoblasts or muscle stem cells in culture. Initially, the cells may be differentially plated on different petri dishes after dissociation and washing as described in Example I. Using a 60 mm petri dish, the cells may first be incubated in complete medium for two to four hours. During this time, epithelial cells will tend to attach quickly to the petri dish while the myoblasts remain in the supernatant. The supernatant may then be collected and the myoblasts may be plated on a different petri dish coated with natural or synthetic biomaterials such as those mentioned in Example I. Myoblasts may be enriched by supplementing the growth media with growth factors such as skeletal muscle growth factor, prostaglandin $F_{2\alpha}$ ("$PGF_{2\alpha}$"), and insulin-like growth factor I ("IGF-1").

Further, myoblasts may be differentiated into specific myoctes or muscle cells by culturing the myoblasts in complete medium or in minimal media (e.g. complete medium less the fetal calf serum) supplemented with muscle specific growth or differentiation factors such as $PGF_{2\alpha}$ at concentrations ranging from 24 pg/ml to 28 pg/ml, and insulin from $10^{-6}$ M to $10^{-5}$ M. To more closely mimic in vivo muscle cells, which are normally innervated by neuronal cells, the culture medium may also be supplemented with appropriate neurotransmitters such as acetylcholine.

EXAMPLE III

Alternatively, myoblasts may be enriched from toti-potent embryonic stem cells. Toti-potent cells may be derived from in vitro fertilized eggs of an animal using in vitro fertilization techniques, from stem cells present in umbilical cords or placenta, or from Embryonic Stem (ES) cells isolated from cells at the blastocyst stage. ES cells, for example, may be collected, gently dissociated by trypsin, and cultured in vitro with recombinant leukemia inhibitory factor (Chemicon, San Diego, Calif.) and feeder cells such as growth arrested embryonic fibroblasts cells. These toti-potent cells may be treated with growth factors such as $PGF_{2\alpha}$ or IGF-1 to induce the cells to differentiate into myoblasts.

EXAMPLE IV

Using standard immunohistochemistry or in-situ hybridization techniques, myoblasts or myocytes (differentiated muscle cells) may be identified. Briefly, myoblasts or myocytes grown in culture may be transferred into glass slides coated with appropriate extracellular matrix as described above. These cells may be grown to the desired number and differentiation using the conditions described above. After a sufficient growth and differentiation period, the cells may be fixed with 4% formaldehyde. If intracellular antibody markers or nucleotide probes are to be used, the cell membranes may be permeabilized with 1% NP-40 or Triton-X. Antibodies against markers specific for myoblasts or myocytes such as myosin, titin, alpha-actinin available from Sigma® may be used to identify the cells using standard fluorescent immunohistochemistry techniques. Alternatively, single stranded RNA or DNA probes for these markers may also be used for in-situ hybridization.

In addition, when the muscle cells have been attached to a three dimensional support structure as disclosed below, they may be cryo-frozen, sectioned and identified using antibody markers such as antibodies against myosin, titin, 12101, troponin T, alpha actinin available from Sigma®.

EXAMPLE V

Two or three dimensional scaffolds or supports may be sculpted from natural biomaterials (e.g. collagen, fibronectin, laminin, or other extracellular matrix) or synthetic biomaterials (e.g. hydroxyapatite, alginate, polyglycolic acid, polylactic acid, and their copolymers), or both. Preferably, the three dimensional scaffolds are sculpted with branch pathways for nutrients and culture media to reach the internal mass of the forming muscle tissues. Examples of materials and construction methods for these scaffolds are provided by U.S. Pat. No. 5,686,091, entitled "Biodegradable Foams For Cell Transplantation"; U.S. Pat. No. 5,863,984, entitled "Biostable Porous Material Comprising Composite Biopolymers"; U.S. Pat. No. 5,770,417, entitled "Three-Dimensional Fibrous Scaffold Containing Attached Cells for Producing Vascularized Tissue in vivo;" and U.S.

Pat. No. 5,916,265, entitled "Method of Producing a Biological Extracellular Matrix for Use as a Cell Seeding Scaffold and Implant." These patents are hereby incorporated by reference as if fully set forth herein.

The support structure is preferably sculpted to different sizes, shapes, and forms to allow for growth of muscle tissues resembling different types of meat products such as steak, tenderloin, shank, chicken breast, drumstick, lamb chops, fish fillet, lobster tail, etc.

EXAMPLE VI

Adipocytes, chondrocytes, and ostooblasts are all capable of differentiating from pluri-potent mesenchymal stem cells or toti-potent embryonic stem cells. The stem cells may be isolated as described in Example I or III. The stem cells may be cultured in DMEM, or Ham's F-12, or both in a 1:1 ratio. The medium may be supplemented with thyroid hormone, transferrin, insulin, as well as other growth factors, such as insulin-like growth factor (IGF), basic fibroblast growth factor, and growth hormone.

For adipocytes, differentiation may be achieved by treating the stem cells with bone morphogenetic proteins ("BMP") such as BMP-4 and BMP-2, which are known to induce commitment to the adipocyte lineage. Ahrens et. al., *Expression of human bone morphogenetic proteins-2 or -4 in murine mesenchymal progenitor C3H10T1/2 cells induces differentiation into distinct mesenchymal cell lineages*, DNA Cell Biol., 12:871–880 (1993); Wang et. al., *Bone Morphogenetic protein-2 causes commitment and differentiation in C3H10T1/2 and 3T3 cells*. Growth Factors 9:57 (1993). These references are hereby incorporated by reference as if fully set forth herein.

In addition to BMPs, the differentiation of adipocytes may be enhanced with agonist of peroxisome proliferator-activated receptor gamma ("PPAR gamma") such as BRL 49653 (rosiglitazone). Sottile and Seuwen, *Bone morphogenetic protein-2 stimulates adipogenic differentiation of mesenchymal precursor cells in synergy with BRL 49653 9 (rosiglitzaone)*, FEBS Lett, 475(3):201–204 (2000). This reference is hereby incorporated by reference as if fully set forth herein.

In certain situations, myoblasts may even be induced to trans-differentiate into adipoblasts (adipocyte precursors) by treating myoblasts cells or muscle satellite cells with long-chain fatty acids ("LCFA") or thiazolidinediones, or both Grimaldi et. al., *Trans-differentiation of myoblasts to adipoblasts: triggering effects of fatty acids and thiazolidinediones*, Prostaglandins Leukot Essent Fatty Acids, 57(1):71–75 (1997); Teboul et. al., *Thiazolidinediones and fatty acids convert myogenic cells into adipose-like cells*, J. Biol. Chem. 270(47):28183–28187 (1995). These references are hereby incorporated by reference as if fully set forth herein.

Thus, meat products with the desired amount of fat content may be produced by seeding and co-culturing muscle cells and adipocyte cells at a certain ratio. Alternatively, stem cells may be allowed to differentiate initially into myoblasts and then at a later time, LCFA or thiadolidinediones may be added at different concentrations and different exposure times to trans-differentiate the myoblasts into adipocytes as desired. Furthermore, the growth of muscle cells and fat cells may be regulated by controlling the concentration of the growth and differentiation factors. For example, if less fat cells are desired in the final meat product, lesser concentrations of BMP factors may be added to the culture while a higher concentration of $PGF_{2\alpha}$ and/or insulin may be added to promote muscle cell growth.

EXAMPLE VII

Chondrocytes or cartilage cells may also be isolated from an animal's knee or rib cages. Using similar techniques as described in Example I, dissected tissue from the knee or rib cages may be minced, digested with collagenase, and washed with complete medium. The cells may then be differentially plated to increase the purity of chondrocyte cells.

It is known that chondrocytes differentiate in response to mechanical stress. Thus, preferably, the cells may be subjected to shear flow stress as described in U.S. Pat. No. 5,928,945, entitled "Application of Shear Flow Stress to Chondrocytes or Chondrocyte Stem Cells to Produce Cartilage," which is hereby incorporated by reference as if fully set forth herein.

Chondrocytes may initially form a first layer of support cells in a three-dimensional scaffold. Myoblasts or adipocyte cells, or both, may then be seeded onto the chondrocyte layer and grown to the desired size. As such, the chondrocyte layer may provide additional adhesion or growth factors to the muscle cells.

EXAMPLE VIII

Muscle cells grown in vitro differ from muscle cells grown in vivo in that in vivo cells are used during exercise or body movements. As muscles are used in vivo, muscle cells, in limbs for example, contract and relax in accordance with the movement of the limbs. Hence, to more closely mimic the growth of muscle cells in vivo, the cells grown in vitro may be exposed to an electric or oscillating current, or pulses of electric or oscillating current to contract the muscle cells. Electric probes may be immersed into the culture media to deliver mild current. Alternatively, the support structure may be coated with electrically conducting materials. Examples of electrically conducting materials and a method for coating them onto the support structure are described in U.S. Pat. No. 5,843,741, entitled "Method for Altering the Differentiation of Anchorage Dependent Cells on an Electrically Conducting Polymer," which is hereby incorporated by reference as if fully set forth herein.

The preceding examples illustrate the procedures for producing meat products ex vivo. They are intended only as examples and are not intended to limit the invention to these examples. It is understood that modifying and combining the examples above do not depart from the spirit of the invention.

What is claimed is:

1. A method of providing nutrition to a subject comprising providing the subject with a non-human meat product produced by the following steps:
    culturing non-human muscle cells ex vivo;
    seeding the non-human muscle cells onto a support structure; and
    growing the non-human muscle cells to produce said non-human meat product, wherein said non-human meat product is suitable for consumption, and wherein said subject consumes said non-human meat product to obtain nutrition therefrom.

2. The method in claim 1 further comprising the step:
    exposing the non-human muscle cells to an electric or oscillating current.

3. The method in claim 1 further comprising the step:
    adding nutrients to be incorporated into the non-human meat products.

4. The method in claim 1 wherein the non-human muscle cells are derived from animals selected from the group consisting of mammals, birds, fishes, invertebrates, reptiles, and amphibians.

5. At The method in claim 1 wherein the non-human meat product is substantially free from harmful microbial contamination.

6. The method in claim 1 wherein the non-human muscle cells are skeletal muscle cells.

7. The method in claim 1 wherein the non-human muscle cells are derived from pluripotent or totipotent non-human stem cells.

8. The method of claim 1 further comprising the step:

seeding non-human fat cells onto said support structure, wherein said non-human fat cells grow in conjunction with said non-human muscle cells to produce said non-human meat product.

9. The method of claim 8 wherein said non-human fat cells are derived from pluripotent or totipotent non-human stem cells.

10. The method of claim 1 further comprising the step:

seeding non-human cartilage cells onto said support structure, wherein said non-human cartilage cells grow in conjunction with said non-human muscle cells to produce said non-human meat product.

11. The method of claim 10 wherein said non-human cartilage cells are derived from pluripotent or totipotent non-human stem cells.

\* \* \* \* \*